United States Patent
Galen et al.

(10) Patent No.: US 6,670,192 B1
(45) Date of Patent: Dec. 30, 2003

(54) APPARATUS FOR COMBINED ASSAY FOR CURRENT GLUCOSE LEVEL AND INTERMEDIATE OR LONG-TERM GLYCEMIC CONTROL

(76) Inventors: Robert S. Galen, 20101 N. Park Blvd., Shaker Heights, OH (US) 44118; John F. Burd, 5659 Glenstone Way, San Diego, CA (US) 92121; Talei Hoblitzell, 8894-B Highwood Dr., San Diego, CA (US) 92119; Gebhard Neyer, 2750 Circullo Santiago #K, Carlsbad, CA (US) 92008

(*) Notice: Subject to any disclaimer, the term of this patent is extended or adjusted under 35 U.S.C. 154(b) by 0 days.

(21) Appl. No.: 09/477,900

(22) Filed: Jan. 5, 2000

Related U.S. Application Data

(60) Continuation of application No. 08/764,320, filed on Dec. 12, 1996, now Pat. No. 6,027,692, which is a division of application No. 08/418,495, filed on Apr. 7, 1995, now Pat. No. 5,695,949.

(51) Int. Cl.$^7$ ............................................. G01D 33/72
(52) U.S. Cl. ................. 436/67; 422/56; 422/57; 422/61; 435/970; 435/287.7; 435/287.9; 435/14; 436/828; 436/67; 436/86; 436/95
(58) Field of Search .......................... 422/56, 57, 61; 435/14, 970, 287.7, 287.9; 436/828, 67, 86, 95

(56) References Cited

U.S. PATENT DOCUMENTS

| | | | |
|---|---|---|---|
| 3,552,929 A | 1/1971 | Fields et al. | 23/253 |
| 3,802,842 A | 4/1974 | Lange et al. | 23/253 |
| 3,809,605 A | 5/1974 | Schmitt et al. | 162/158 |
| 3,897,214 A | 7/1975 | Lange et al. | 23/253 |

(List continued on next page.)

FOREIGN PATENT DOCUMENTS

| | | | |
|---|---|---|---|
| EP | 283285 | * | 9/1987 |
| EP | 0388782 | | 9/1990 |
| EP | 0473189 A2 | | 3/1992 |
| WO | WO 96/00897 | | 1/1996 |

OTHER PUBLICATIONS

Armbruster, "Diabetes mellitus, protein glycation, and laboratory assays for monitoring long–term glycemic control." *Clinical Laboratory Science*, 3(3):184–188 (1990).

Armbruster, "Fructosamine: Structure, Analysis, and Clinical Usefulness." *Clinical Chemistry*, 33(12):2153–2163 (1987).

Baker et al., "Clinical usefulness of estimation of serum fructosamine concentration as a screening test for diabetes mellitus." *British Med. J.*, 287:863–867 (1983).

Benjamin and Sacks, "Glycated protein update: implications of recent studies, including the diabetes control and complications trial." *Clin. Chem.*, 40(5):683–687 (1994).

(List continued on next page.)

*Primary Examiner*—Jill Warden
*Assistant Examiner*—Yelena Gakh

(57) ABSTRACT

The present invention is directed to a single test system and method for determining the integrated glycemic condition of a subject by measuring the concentration of glucose and the level of protein-bound glucose in a subject's body fluid, such as whole blood. The glucose concentration is indicative of the subject's immediate glycemic condition, whereas the protein-bound glucose concentration is indicative of either intermediate or long-term glycemic condition. Optionally, other analytes indicative of glycemic condition, such as ketone bodies or fatty acid derivatives, can also be measured. The present invention also provides a method of diagnosing diabetes. The invention additionally provides a method for analyzing the concentration of fructosamine in less than or equal to five minutes without the use of a reaction accelerator.

16 Claims, 6 Drawing Sheets

U.S. PATENT DOCUMENTS

| | | | | |
|---|---|---|---|---|
| 3,907,503 A | * | 9/1975 | Betts et al. | 356/39 |
| 3,973,849 A | | 8/1976 | Jackson et al. | 356/97 |
| 4,042,335 A | | 8/1977 | Clement | 23/253 |
| 4,050,898 A | | 9/1977 | Goffe, deceased et al. | 23/253 |
| 4,223,995 A | | 9/1980 | Fletcher | 356/418 |
| 4,269,605 A | | 5/1981 | Dean et al. | |
| 4,397,956 A | | 8/1983 | Maggio | 436/34 |
| 4,478,744 A | | 10/1984 | Mezei et al. | |
| 4,482,251 A | | 11/1984 | Saylor | 356/418 |
| 4,545,382 A | | 10/1985 | Higgins et al. | 128/635 |
| 4,642,295 A | | 2/1987 | Baker | 436/87 |
| 4,645,742 A | | 2/1987 | Baker | 436/15 |
| 4,681,444 A | | 7/1987 | Ferber et al. | 356/318 |
| 4,729,657 A | | 3/1988 | Cooper et al. | 356/319 |
| 4,744,657 A | | 5/1988 | Aralis et al. | 356/319 |
| 4,748,114 A | * | 5/1988 | Kallies et al. | 422/56 |
| 4,797,256 A | * | 1/1989 | Watlington | 422/58 |
| 4,806,468 A | | 2/1989 | Wagner et al. | 435/7 |
| 4,852,025 A | | 7/1989 | Herpchbohm | 364/551.01 |
| 4,935,346 A | | 6/1990 | Phillips et al. | 435/14 |
| 4,956,301 A | | 9/1990 | Ismail et al. | 436/87 |
| 4,999,582 A | | 3/1991 | Parks et al. | |
| 5,002,893 A | | 3/1991 | Rosenthal | 436/87 |
| 5,049,487 A | | 9/1991 | Phillips et al. | 435/4 |
| 5,059,394 A | | 10/1991 | Phillips et al. | 422/68.1 |
| 5,075,077 A | | 12/1991 | Durley, III et al. | 436/170 X |
| 5,110,745 A | * | 5/1992 | Kricka et al. | 436/87 |
| 5,169,787 A | | 12/1992 | Knappe et al. | 436/169 |
| 5,179,005 A | | 1/1993 | Phillips et al. | 435/14 |
| 5,183,739 A | | 2/1993 | Cohen | 435/7.23 |
| 5,206,144 A | | 4/1993 | Zeuthen et al. | 435/7.25 |
| 5,215,716 A | | 6/1993 | Arai | |
| 5,223,219 A | | 6/1993 | Subramanian et al. | 422/55 |
| 5,223,392 A | * | 6/1993 | Cohen | 435/329 |
| 5,242,842 A | * | 9/1993 | Sundrehagen | 436/161 |
| 5,243,516 A | | 9/1993 | White | |
| 5,258,163 A | | 11/1993 | Krause et al. | 422/58 |
| 5,271,895 A | | 12/1993 | McCroskey et al. | 422/58 |
| 5,281,395 A | | 1/1994 | Markart et al. | 422/82.05 |
| 5,284,777 A | | 2/1994 | Rosenthal et al. | 436/518 |
| 5,304,468 A | | 4/1994 | Phillips et al. | |
| 5,366,868 A | | 11/1994 | Sakamoto | |
| 5,384,239 A | * | 1/1995 | Saunders | 435/329 |
| 5,470,752 A | | 11/1995 | Burd et al. | |
| 5,571,723 A | | 11/1996 | Evans et al. | |
| 2003/0068830 A1 | * | 4/2003 | McCroskey et al. | 436/518 |

OTHER PUBLICATIONS

Caines et al., "Colorimetric determination of non–enzymatically glycated albumin." *Clinical Biochemistry*, 19:26–30 (Feb. 1986).

Candiloros, "Decreased Erythrocyte Membrane Fluidity in Poorly Controlled IDDM." *Diabetes Care*, 18(4) 549–551 (1995).

Cefalu et al., "Serum fructosamine as a screening test for diabetes in the elderly: a pilot study." *JAGS*, 41:1090–1094 (1993).

Dix et al., "Glycohemoglobin and glucose tolerance tests compared as indicators of borderline diabetes." *Clin. Chem.*, 25(6):877–879 (1979).

Dods and Bolmey, "Glycosylated hemoglobin assay and oral glucose tolerance test compared for detection of diabetes mellitus." *Clin. Chem.* 25(5):764–768 (1979).

Goldstein et al., "Is glycohemoglobin testing useful in diabetes mellitus? Lessons from the diabetes control and complications trial." *Clin. Chem.*, 40(8):1637–1640 (1994).

Goldstein and Little, "The impact of the diabetes control and complications trial on the clinical laboratory." *Viewpoints*, 4 (1993).

Guillausseau et al., "Comparison of HbA$_1$ and fructosamine in diagnosis of glucose–tolerance abnormalities." *Diabetes Care* 13(8):898–890 (1990).

Johnson et al., "Fructosamine: a new approach to the estimation of serum glycosylprotein. An index of diabetic control." *Clinica Chimica Acta*, 127:87–95 (1982).

Kahn, "Tight blood glucose control shown beneficial for diabetes." *Clin. Chem. News*, 19(9) (1993).

Larsen et al., "Effect of long–term monitoring of glycosylated hemoglobin levels in insulin–dependent diabetes mellitus." *New England J. of Med.*, 323(15):1021–1025 (1990).

Pamphlet Insert to the Abbott Vision System, (1993).

Pamphlet Insert to the Lifescan, ONE TOUCH II Blood Glucose Meter, (1990).

Rosen, "Protein–Bound glucose as a screening test for diabetes." *Hospital Practice*, 27:59–61 (1992).

Rowe DJF, "The Measurement and Clinical Significance of Glycated Proteins." *Practical Diabetes*, 6(6) 256–260 (1989).

Shima et al., "The relative value of glycated albumin, hemoglobin A$_{1c}$ and fructosamine when screening for diabetes mellitus." *Diabetes Research and Clin. Practice*, 7:243–250 (1989).

Searcy and Bolland, "Fructosamine: The next step in diabetic management." *Amer. Clin. Lab.* 12(8) 1993.

Salemans et al., "The value of HbA$_1$ and fructosamine in predicting impaired glucose tolerance—an alternative to OGTT to detect diabetes mellitus or gestational diabetes." *Ann. Clin. Biochem.*, 24:447–452 (1987).

* cited by examiner

APPARATUS FOR COMBINED ASSAY FOR CURRENT GLUCOSE LEVEL AND INTERMEDIATE OR LONG-TERM GLYCEMIC CONTROL

This application is a continuation of application Ser. No. 08/764,320 now U.S. Pat. No. 6,027,692, filed Dec. 12, 1996, which is a division of application Ser. No. 08/418,495 now U.S. Pat. No. 5,695,949, filed Apr. 7, 1995.

BACKGROUND OF THE INVENTION

1. Field of the Invention

This invention relates to an assay system, and more specifically, to determining the integrated glycemic condition of a diabetic by measuring glucose and protein-bound glucose concentration levels.

2. Background Information

Individuals suffering from diabetes mellitus have an abnormally high blood sugar level generally because the pancreas does not secrete sufficient amounts of the active hormone insulin into the bloodstream to regulate carbohydrate metabolism. If an abnormally high blood sugar level, known as a hyperglycemic condition, is allowed to continue for prolonged periods, the individual will suffer from the chronic complications of diabetes, including retinopathy, nephropathy, neuropathy and cardiovascular disease. Studies indicate that diabetic patients who are able to maintain near normal glycemic control greatly reduce the likelihood of these dire complications. Therefore, several tests have been developed to measure and control glycemic condition.

One common medical test to control glycemic condition is the direct measurement of blood glucose levels by diabetics. Because blood glucose levels fluctuate significantly throughout a given day, being influenced by diet, activity, and treatment, depending on the nature and severity of the individual case, some patients measure their blood glucose levels up to seven times a day. Based on the observed pattern in the measured glucose levels, the patient and physician together make adjustments in diet, exercise and insulin intake to better manage the disease. Clearly, this information should be available to the patient immediately.

However, because of the frequent fluctuation of glucose levels in a given day, tests which are independent of a patient's diet, activity, and/or treatment and which provide longer term indications of blood glucose levels have also been developed. These tests measure the concentration of glycated proteins or "protein-bound glucose" (PBG). Proteins, such as those present in whole blood, serum and other biological fluids react with glucose, under non-enzymatic conditions, to produce glycated proteins. The extent of the reaction is directly dependent upon the glucose concentration of the blood.

One of the first glycated protein tests developed measures glycated hemoglobin, namely Hemoglobin $A_{1c}$ ($HbA_{1c}$), which reflects glycemic control over approximately a 2 to 3 month period. Other such tests measure serum proteins, such as total glycated serum protein, or a specific glycated serum protein, namely glycated albumin. Glycated albumin reflects an intermediate glycemic control over approximately a 2 to 3 week period.

Yet another way to indirectly assess blood sugar concentration is to analyze fructosamine concentration. Glycated proteins are also known as fructosamines or ketoamines. The blood proteins are glycated in vivo by a non-enzymatic reaction between glucose and available amino groups of blood proteins, principally the $\epsilon$-amino groups of lysine residues and the $\alpha$-amino groups of the protein's terminal amino acid. The glucose binds to an amino group of the protein to form a Schiff base, i e., a glucosylamine or aldimine, that undergoes molecular rearrangement to form a stable ketoamine. This reaction sequence is illustrated in FIG. 1a. In the art, such ketoamines are generically known as "fructosamines." The degree of protein glycation and fructosamine formation is directly proportional to blood glucose concentration. Measurement of serum or plasma fructosamine levels is useful for monitoring diabetic control because fructosamine concentrations in serum or plasma reflect an average of blood glucose level over approximately a half month period.

While these individual tests to directly and indirectly measure glucose have been developed, there is no convenient test system available which allows a diabetic patient or a physician to assess both the immediate glucose level as well as an intermediate or long-term glycemic condition. Currently, the glucose test is routinely run by the doctor or the patient, however, the glycated protein testing is typically performed in a clinical lab using complicated techniques and expensive instrumentation. Results from these clinical lab tests are usually not available to the doctor and patient for several days. This delay in information transfer decreases the value of the test result. The physician can even neglect to relay the test result to the patient until the next visit, which could be several months. Scandinavian investigators recently showed that doctors and patients who were made aware of their glycated protein test results had better glycemic control than those who were unaware of such results. It is also now believed that glycated proteins can be the causative agents in disease complications. Therefore, a need exists for conveniently and quickly measuring glycated protein alone, or in combination with glucose for determining the integrated glycemic condition of a subject.

Currently, no test system exists which determines the integrated glycemic condition of a subject, providing the subject with a complete picture of his or her glycemic status, thus allowing for the best possible monitoring and treatment. Particularly useful would be a single instrument for determining a subject's integrated glycemic condition which could be used at the doctor's office, or better yet, at home by the diabetic patient. The present invention satisfies these needs and provides related advantages as well.

SUMMARY OF THE INVENTION

The present invention is directed to a single test system and method for determining the integrated glycemic condition of a subject by measuring the concentration of glucose and the level of protein-bound glucose in a subject's body fluid, such as whole blood. The glucose concentration is indicative of the immediate glycemic condition of the subject, whereas the protein-bound glucose concentration is indicative of either intermediate or long-term glycemic condition. Optionally, other analytes related to the glycemic condition, such as ketone bodies or fatty acid derivatives, can also be measured. The present invention also relates to a method of diagnosing diabetes.

The invention also provides a method for analyzing the concentration of fructosamine in less than or equal to five minutes, even in the absence of a reaction accelerator.

BRIEF DESCRIPTION OF THE DRAWINGS

FIG. 4 also shows an embodiment of the apparatus which is capable of determining the concentration levels of fructosamine and glucose in the body fluid sample applied to the respective test devices.

DETAILED DESCRIPTION OF THE INVENTION

Figure 1A:
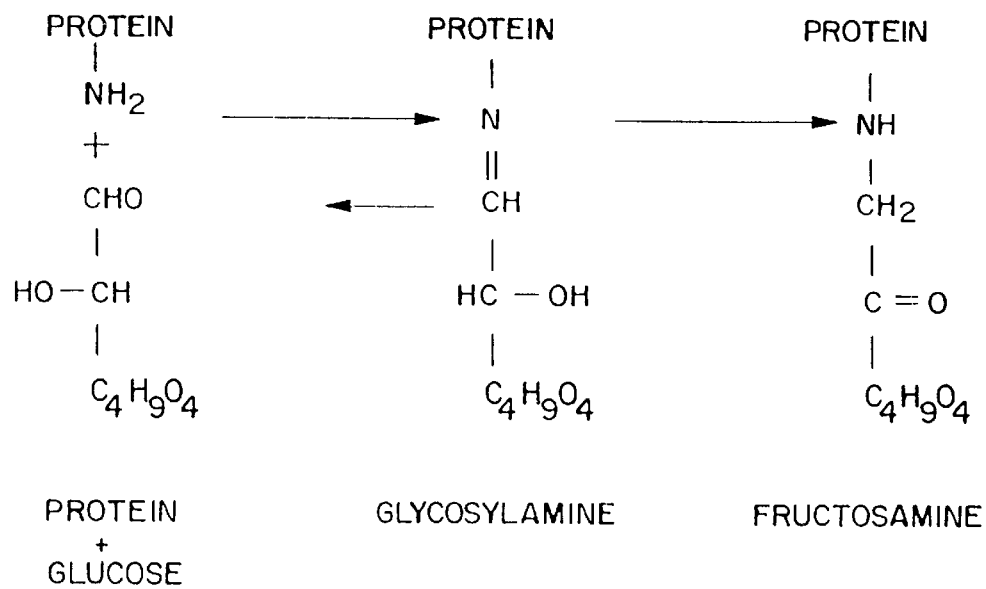
FIG. 1a provides the reaction sequence for the formation of fructosamines in vivo.

The methods and single test system of the present invention provide a combined assay which allows a diabetic patient or a physician to assess the subject's current glucose level as well as the subject's intermediate or long-term glycemic condition. Such a system is useful for diabetic patients and their physicians in the quest to normalize their glycemic control, thereby reducing the possibility of severe disease complications. Prior to this invention the complete glycemic condition of a patient could only be derived from separate tests and frequently the glycated protein test had to be performed in a clinical laboratory. The present test system allows the doctor to perform a combined test for glucose and protein-bound glucose at the office, or even better, it allows the diabetic patient to perform the testing at home, thereby providing a quick, accurate, and complete picture of the patient's glycemic condition. The present invention provides a single test system and method for determining the integrated glycemic condition of a subject by testing for both glucose and protein-bound glucose. The information provided by testing for both glucose and protein-bound glucose is particularly useful since glucose concentration can fluctuate widely in diabetic patients and these fluctuations would be missed by the standard glucose test regimen.

As used herein, the term "integrated glycemic condition" means the immediate glucose concentration in combination with the average glucose concentration over a period of time. "Immediate" means the current glucose level in a subject's body fluid at the time of measurement. Glucose concentration over time is indicative of either intermediate or long-term glycemic condition and can be determined by measuring the concentration of protein-bound glucose. Intermediate glycemic condition is generally on the order of days to approximately one month, for example as indicated by the measurement of fructosamine which reflects an average glucose concentration in the body fluid over approximately a half month period. Long-term glycemic condition reflects glycemic status well over a month, generally a 2 to 3 month period. In the present invention, the order of measuring glucose, protein-bound glucose, and any additional analytes indicative of glycemic condition is irrelevant. For example, fructosamine concentrations can be measured first and glucose levels second. Regardless of the order, the invention always provides the integrated glycemic condition of a subject.

In addition to using the present invention for monitoring the glycemic condition of a subject known to have diabetes, the present invention can also be used as a diagnostic for diabetes. The present invention can be used for diagnosing or screening individuals suspected of, or who can be prone to, having diabetes. For example, a subject who may be prone to diabetes, and for which screening is necessary, could be a pregnant woman. Other individuals for which diagnosis can be particularly useful are relatives of known diabetics.

The method of diagnosing diabetes in a subject using the single test system of the present invention involves, first, obtaining at least one body fluid sample from a subject, then measuring the concentration of glucose in a body fluid sample from the subject and measuring the concentration of protein-bound glucose in a body fluid from the subject. The order of measuring glucose and protein-bound glucose is irrelevant. Finally, the measured concentrations of glucose and protein-bound glucose are compared to glucose concentrations and protein-bound-glucose concentrations of a normal subject.

Combined high glucose levels and high protein-bound glucose concentration, or protein-bound glucose levels which are indicative of high glucose levels over a period of time, as compared to those of a normal subject is diagnostic or indicative of diabetes. For example, a normal subject has fasting glucose levels in the range of 70–120 mg/dl. Glucose levels above 120 mg/dl can be indicative of diabetes. Levels of glucose above 150 mg/dl are strongly indicative of diabetes and above 200 mg/dl almost unquestionably indicates a diabetic condition. A normal subject has PBG concentration levels on the order of 2 to 3 milliMolar (mM), whereas levels of PBG above 3 mM, in combination with high glucose levels, can be diagnostic of diabetes.

The advantage of the combined assay of the present invention is that until recently serum glucose was the only screening test available for possible diabetes. An abnormally high serum glucose is not definitive, however, it could be due to diabetes, but it could also reflect nonfasting, stress, or the ingestion of certain drugs. Given the shortcomings of glucose testing alone Rosen et al., *Hospital Practice*, 27:59–61 (1992), tested several patient serum samples for both glucose and protein-bound glucose as a means of screening for diabetes. The present invention, however, has the added advantage of being capable of testing an unprocessed body fluid sample or samples which do not require separation and the like prior to testing. For example, drops of whole blood from a patient, without separation of serum or plasma prior to testing, can be used with the present methods and test system. The simplicity and convenience of the present invention thus allows doctors and patients to know the integrated glycemic condition of the patient within minutes, either at the doctor's office or at home.

As used herein the term "protein-bound glucose," or "PBG," encompasses any glycated protein or combination thereof. PBG concentration correlates to glucose concentration over time. The PBG test, or non-glucose test, for glycemic condition can include tests for total or individual glycated proteins found in body fluids. For example, one can measure "total glycated hemoglobin," which includes all species of hemoglobin glycated, or one can measure a specific hemoglobin, such as Hemoglobin $A_{1c}$ ($HbA_{1c}$).

Similarly, one can measure all serum glycated proteins, or "total glycated serum protein," or a specific glycated serum protein, such as glycated albumin. In addition, "protein-bound glucose" encompasses fructosamines. More than one PBG can be measured in the present invention. For example, fructosamine can be measured as an indication of intermediate glycemic condition and $HbA_{1c}$ can be measured as an indication of long-term glycemic condition.

The major normal hemoglobin species are $A_0$ ($\alpha_2\beta_2$), $A_2$ ($\alpha_2$ $\delta_2$), and F($\alpha_2$ $\gamma_2$). A variety of minor, but normally occurring, hemoglobin variants exist and are generally referred to as $HbA_1$, or "fast" hemoglobins as they migrate in advance of $A_0$ on an electrophoretic gel. The family of $HbA_1$ includes $A_{1a1}$, $A_{1a2}$, $A_{1b1}$, $A_{1b2}$, $A_{1b3}$, $A_{1c}$, $A_{1d}$, and $A_{1e}$, all of which are glycated hemoglobins. All fractions are typically elevated in the diabetic state compared with the concentrations in the nondiabetic population. $HbA_{1c}$ is the major subfraction, but all of these fractions generally vary with the mean blood glucose concentration and reflect the state of glycemic control. Most hemoglobins become glycated, generally through a reaction between glucose and the $\epsilon$-amino groups of lysine residues in hemoglobin. $HbA_{1c}$, in contrast, binds to glucose through its amino-terminal valine residue. The half-life of hemoglobin is about 60 days, therefore, measurement of total glycated hemoglobin or $HbA_{1c}$ is indicative of long-term glycemic condition, generally reflecting approximately a 2 to 3 month period.

Glycation is not unique to hemoglobin but can occur with serum proteins. Since amino groups react with glucose, most proteins present in body fluids become glycated, including enzymes, immunoglobulins, and most other classes of proteins as well as individual proteins. The total of all serum glycated proteins, or "total glycated serum protein," can be analyzed or a specific glycated serum protein, such as glycated albumin, can be measured. Glycated serum protein measurements, whether total glycated serum protein or an individual glycated serum protein, are indicative of an intermediate glycemic condition. Glycated albumin has a half-life of approximately two to three weeks, while that for other serum proteins can range from two and a half to twenty-three days. Measurement of total glycated serum protein or glycated albumin, therefore, is indicative of an intermediate glycemic condition, reflecting glucose concentrations over a period of a couple days up to approximately one month.

Figure 1B:
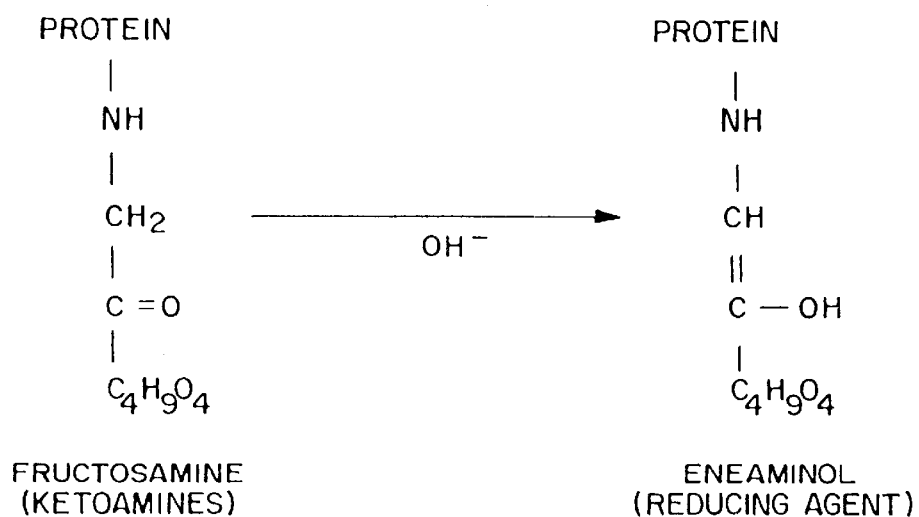
FIG. 1b shows that under alkaline conditions fructosamine forms an eneaminol, a reducing agent, that can be measured, for example, calorimetrically.

Fructosamines are formed by glycated proteins. Glucose binds to an amino group of the protein to form a Schiff base, i.e., a glycosylamine or aldimine, that undergoes molecular rearrangement to form a stable ketoamine. This reaction sequence is illustrated in FIG. 1a. In the art, such ketoamines are generically known as "fructosamines." Since fructosamine formation is directly dependent upon glucose concentration, diabetic individuals have higher fructosamine concentrations in the blood as compared to non-diabetic individuals. Under alkaline conditions, the fructosamines that form in the blood are converted to eneaminols as shown in FIG. 1b. The eneaminol form of fructosamine is a chemically active reducing substance that reacts with a suitable indicator capable of being reduced by fructosamine. For example, the color transition of a chromogenic dye or the fluorescence of a fluorescent reagent resulting from this reaction can be measured and compared with a standard to give an indication of the average glucose concentration in blood samples over the prior half month period. In general, the fructosamine concentration in a body fluid, such as blood serum, reflects an average glucose concentration over a period of approximately a half month.

Optionally, other analytes indicative of glycemic condition, such as ketone bodies, or fatty acid derivatives, can also be measured. During insulin deficiency, as can occur between therapeutic insulin injections as a result of metabolism of insulin, energy needed to sustain cellular function cannot be derived sufficiently from glucose, the chief source of energy for cells. In this situation, the fatty acid oxidation pathways are called upon to supply alternate energy sources. Byproducts from this metabolic process, including ketone bodies, such as acetone, $\beta$-hydroxybutyrate and acetoacetate, fatty acid metabolites and the like, can be detected in blood and other body fluids when the fatty acid metabolizing pathways are activated. Since these analytes are not cleared from the blood immediately when the blood glucose level is restored to a normal level, they provide a short term indication of the state of glucose metabolism in the patient. Such analytes are present in the body fluid in response to changes in the glucose metabolism of a diabetic within from about five minutes (5) to about twelve (12) hours of such change. These optional measurements for additional analytes which are also indicative of glycemic condition can be done in connection with the present invention by methods which are well known in the art. For instance, test reagent strips capable of measuring ketone bodies, as described, for example, in U.S. Pat. No. 4,397,956 to Maggio, can be used in connection with the test system of the instant invention.

An alternative analyte which can optionally be measured and which is also indicative of glycemic status is microalbumin. Microalbumin is present in urine, generally, only when a patient's glycemic condition is so severe as to result in complications associated with the kidney.

The body fluid sample from the subject which is analyzed for glucose and PBG, or other analytes also associated with glycemic condition, can be any unprocessed biological fluid which contains these analytes including, for example, whole blood, urine, saliva, interstitial fluid and tears. The body fluid is "unprocessed," meaning that the body fluid need not be processed, such as by separation techniques and the like, prior to testing. The body fluid can be applied directly to the test device, without, for example, the separation of plasma or 'serum from whole blood. If required, within the test device itself the body fluid can be separated or otherwise processed, such as by a red blood cell separation layer.

The body fluid sample used for measuring the concentration of glucose can, but does not have to, be the same type of body fluid sample as that used for measuring the concentration of PBG. For instance, whole blood can be used for both the glucose portion and the PBG aspect of the invention. Alternatively, the body fluid sample or samples can be different types of body fluids, such as using urine to determine the concentration of glucose and a sample of whole blood to assay for fructosamine. Because the present invention can advantageously be used in the home environment by the patient himself, the preferable body fluid for both the glucose and PBG analysis is whole blood, and more preferably whole blood taken from a finger or earlobe puncture. Although finger sticks are preferred, pipets, droppers, or the like can be used, particularly where a sample is collected.

The body fluid sample or samples from which glucose and PBG are measured can be the same sample or separate samples, depending upon how the sample is taken from the subject. By "separate" samples is meant individual body fluid samples, such as two or more samples, which can, but are not necessarily the same type of body fluid, as described above. For example, where the body fluid samples are each a drop of blood, such as from separate pricks of a subject's finger, they are "separate" or different "samples." Alternatively, the body fluid can be collected from the subject, such as drawing a sample of blood, in which case the body fluid sample for analyzing glucose and PBG would be taken from the collected specimen and are considered the same sample. Additional body fluid samples can be used, such as a third body fluid sample or more, for example, when analyzing more than one PBG or for measuring optional analytes, such as ketone bodies.

The present invention provides measurement of glucose and PBG in a single test system. The system provides a test device containing a signal producing system which is capable of signaling the concentration of glucose present in a body fluid sample 26. The signal producing system is read by an apparatus which has an automatic glucose concentration determining means responsive to the signal produced by the glucose test device 30. The test system of the present invention also includes a test device allowing measurement of the concentration of a PBG. The non-glucose test device 27 contains a signal producing system which is capable of signaling the concentration of a PBG present in a body fluid sample. The signal producing system is read by an apparatus which has an automatic PBG concentration determining means responsive to the signal produced by the PBG test device. A suitable apparatus used in the single test system can read the results of both the glucose test and the PBG test. If optional analytes, also indicative of glycemic condition, are also measured corresponding test devices can be used with the present invention.

Test devices containing signal producing systems capable of signaling the concentration of glucose are well known in the art. Generally, in the art the signal producing system includes reagents which produce a glucose oxidase enzyme reaction. Glucose and glucose oxidase enzyme react to produce hydrogen peroxide. A peroxidase, such as horse radish peroxidase, and a redox indicator, such as o-tolidine, o-dianisidine, 3,3,5,5-tetramethylbenzidine (TMB), 4-aminoantipyrine, and others well known in the art, are capable of being oxidized in the presence of hydrogen peroxide to produce a colored product. A test strip containing these or other reagents of the signal producing system used in analyzing glucose concentration can be prepared by methods well known in the art, such as described in the published European Patent Application 0 388 782 to Chen, and U.S. Pat. No. 5,304,468 to Phillips et al., both of which are incorporated herein by reference.

Figure 3A:
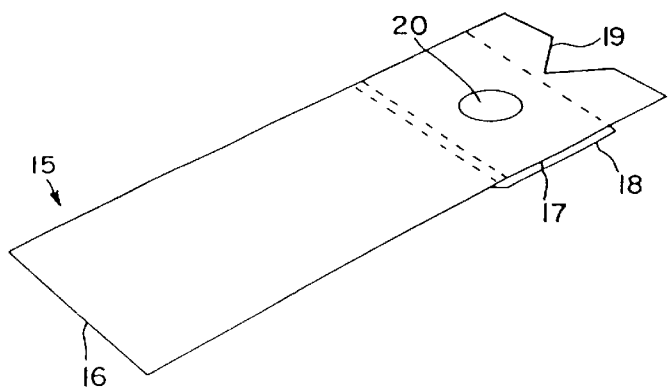
FIG. 3a exemplifies one embodiment of a test device containing a reagent pad to which the body fluid being analyzed is applied.

In a preferred embodiment, as shown in FIG. 3a, the glucose test device 15 has a reagent pad 18 containing the reagent(s) of the signal producing system. The reagent pad 18 is positioned by means of an adhesive 17 at one end of a plastic support member 16 having a notch 19. A more detailed description of materials for the reagent pad(s), the support member(s) and adhesive is provided below in the discussion of the fructosamine test device and is equally applicable to the glucose test device. If required, the glucose test device can additionally contain a blood separation layer, such as the one described below or others well known in the art. Furthermore, other additional layers may optionally be added, such as an interference removal layer, a radiation layer, or others described below or known in the art.

As described above, the test system of the present invention also includes a test device allowing measurement of the concentration of a PBG. The non-glucose test device contains a signal producing system which is capable of signaling the concentration of a PBG present in a body fluid sample. The signal producing system is read by an apparatus which has an automatic PBG concentration determining means responsive to the signal produced by the PBG test device. The signal producing system and reagents used to produce the signal in response to PBG will depend on which PBG analyte is to be measured.

Figure 5:
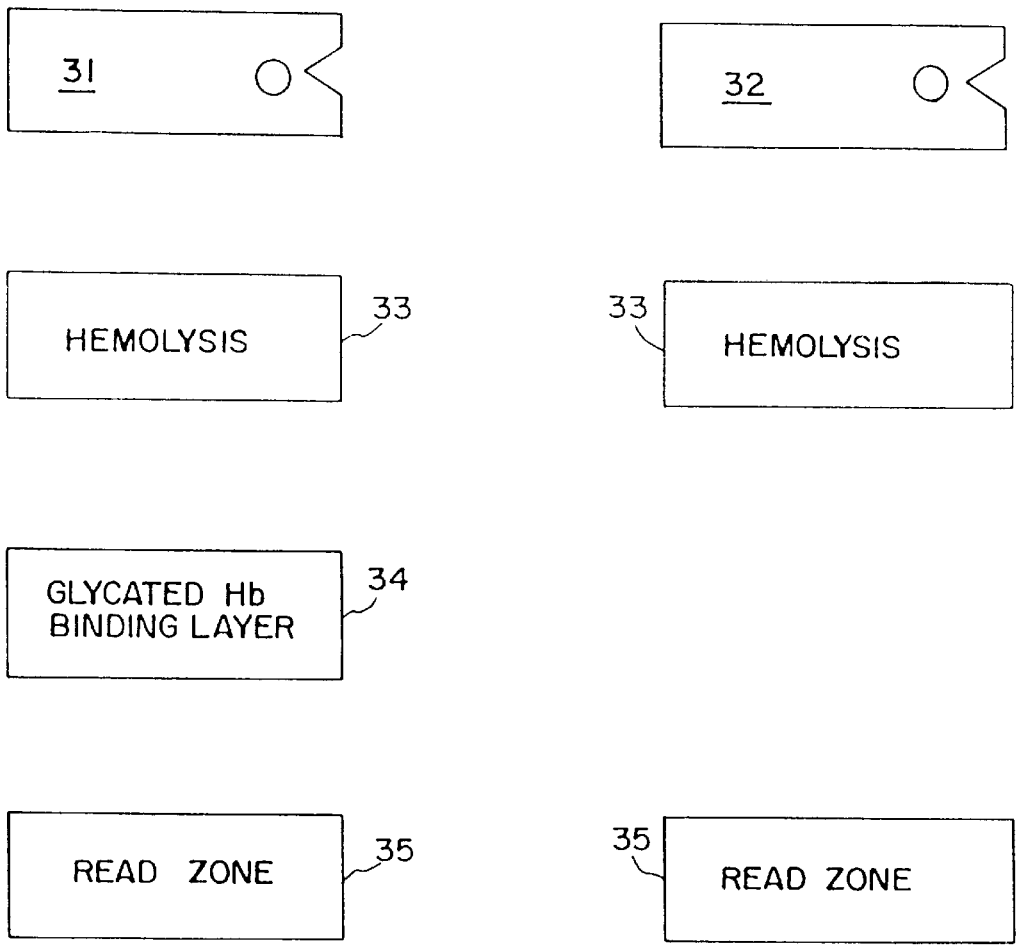
FIG. 5 shows one embodiment of a test device containing two test strips which can be used for measuring glycated hemoglobin in a body fluid sample.

In one embodiment, the PBG test devise comprises two test strips capable of measuring the concentration of glycated hemoglobin in a body fluid sample, particularly blood. This embodiment is exemplified in FIG. 5. With reference to FIG. 5, both test strips, 31 and 32, have a layer containing hemolysis reagents 33 which reagents are capable of lysing red blood cells, thereby liberating hemoglobin. In test strip 31 the hemolysate then passes into a glycated hemoglobin binding layer 34. Any glycated hemoglobin, or "glycohemoglobin," contained in the hemolysate binds to layer 34, whereas all non-glycated hemoglobin passes through to the read zone 35. In test strip 32 there is no glycated hemoglobin binding layer and the hemolysate, including glycated and non-glycated hemoglobin (hereinafter termed "total hemoglobin"), passes directly to the read zone.

In this embodiment of the test device the amount of glycated hemoglobin can be calculated with a suitable apparatus capable of reading test strips 31 and 32 and determining the difference between the two. The amount of glycated hemoglobin can be calculated by subtracting the results obtained from test strip 31 (total hemoglobin minus glycated hemoglobin) from the results of test strip 32 (total hemoglobin).

The hemolysis reagents used in layer 33 can be hemolysins or chemical reagents well known in the art for hemolysis, provided they are reactive with red blood cells when contained on a layer within a test strip. Examples of hemolytic reagents include, for instance saponins, or a variety of detergents, and in particular non-ionic detergents, such as Triton-X-100®.

The glycated hemoglobin binding layer can be, for example, antibodies to glycohemoglobin, such as those described in U.S. Pat. Nos. 4,478,744 to Mezei, 4,806,468 to Wagner et al., 5,183,739 to Cohen and 5,206,144 to Zeuthen et al., each of which is incorporated herein by reference. Alternatively, the glycated hemoglobin binding layer can comprise materials well known for binding glycohemoglobin and commonly used in affinity chromatography, such as phenyl boronic acids, including, for example, m-aminophenyl boronic acid and others as described, for example in U.S. Pat. Nos. 4,269,605 to Dean and 5,284,777 to Rosenthal et al., each of which is incorporated herein by reference. Phenyl boronic acid binds to the cis-diol groups in glucose-modified hemoglobin to form a reversible five-membered ring complex. The boronic acid can be coupled to the layer of the test strip through an agarose or cellulose matrix or by other methods and materials well known in the art, such as those described in the above-identified patents.

The hemoglobin can be monitored in the read zone by simply reading the color of the hemoglobin at 416, 542 or 576 nm. Therefore, the signal producing system capable of signaling the concentration of a PBG, such as hemoglobin, includes direct measurement of the PBG. Additionally, the concentration of hemoglobin can be determined by any of a number of other known methods for measuring hemoglobin. These methods include reaction with potassium ferricyanide and thiocyanate which oxidizes the hemoglobin to methemoglobin and complexes it to form the colored thiocyanmethemoglobin which can be measured at 531 nm. Another known method is the reaction of hemoglobin with cumene hydroperoxide and tetramethylbenzidine. The hemoglobin functions as a peroxidase to catalyze the reaction to produce a colored product which can be measured at either 660 nm or in the near infrared at 890 nm.

In another embodiment, the PBG test device consists of test strips which measure glycated albumin levels. This embodiment can use techniques similar to those employed for measuring glycated hemoglobin in the above embodiment. Here, total albumin, comprising both glycated and non-glycated albumin, is measured on one test strip and on the other test strip total albumin minus glycated albumin is determined. Again, the difference between the two test strips provides the amount of glycated protein of interest.

Figure 6:
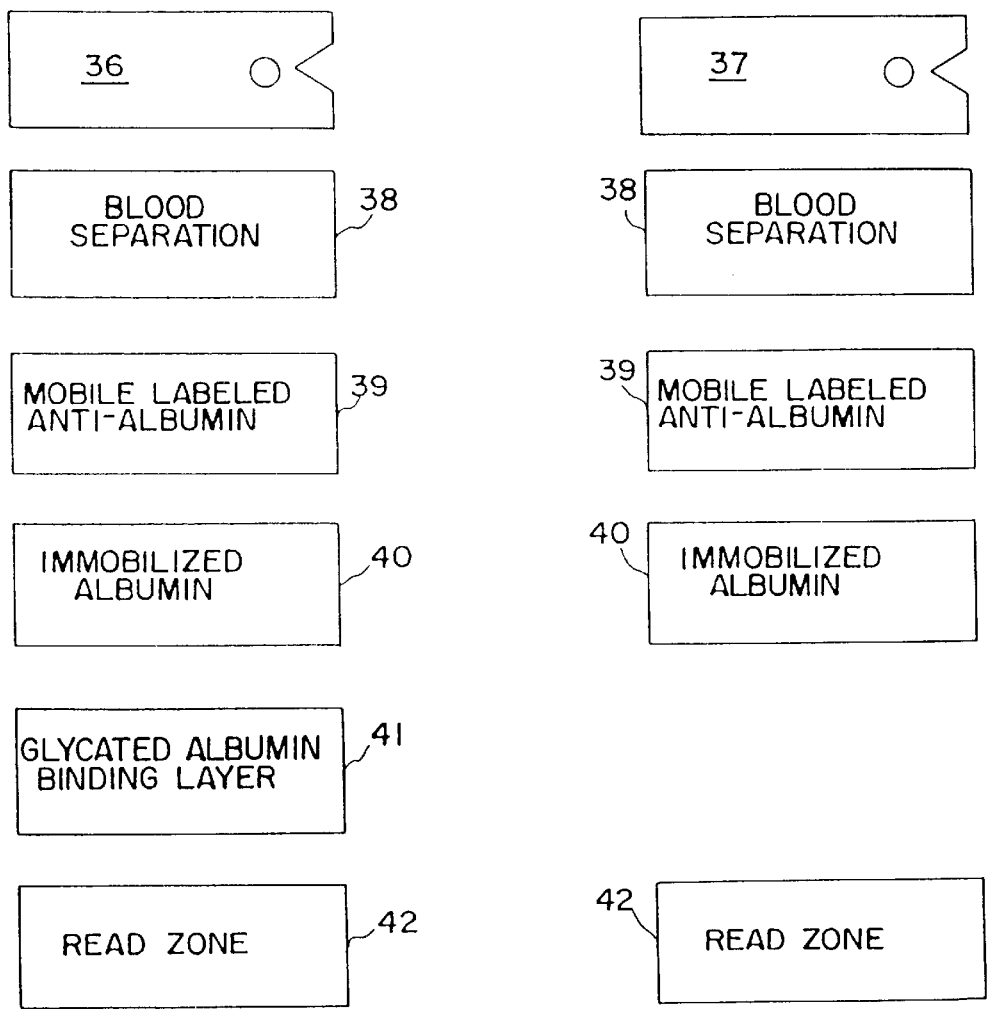
FIG. 6 exemplifies one example of a test device having two test strips which is capable of measuring glycated albumin in a body fluid sample.

For a more detailed description of the test device for measuring glycated albumin, reference is now made to FIG. 6. As shown in FIG. 6, the first layer in both of the test strips, 36 and 37, is a blood separation layer 38 which separates plasma or serum. The separation layer can be similar to the one described in the ensuing Examples or others well known in the art. The separated blood plasma, for example, then goes into the next layer, 39, which is present in both strips and which contains mobile labelled anti-albumin. The labeled albumin antibodies from this layer binds to both the glycated and non-glycated albumin present in the sample and then as a conjugate diffuses into the next layer, the immobilized albumin layer 40. Free mobile labeled antibody from layer 39 which is not bound to albumin diffuses into layer 40 and becomes immobilized to the albumin contained therein. In test strip 36 the conjugate of albumin and labeled anti-albumin then passes into a glycated albumin binding layer 41 where only those conjugates containing glycated albumin become bound. The labeled anti-albumin and non-glycated albumin conjugate in test strip 36 diffuses to the read zone 42 for measurement indicative of total albumin minus glycated albumin. Test strip 37 of the test device does not contain a glycated albumin binding layer and the read zone 42 of test strip 37 is therefore indicative of total albumin. The amount of glycated albumin can be calculated by subtracting the results obtained from test strip 36 (total albumin minus glycated albumin) from the results of test strip 37 (total albumin).

The above described embodiment for measuring glycated albumin, as well as the glycohemoglobin embodiment, can take advantage of techniques and principals similar to those taught by Liotta in U.S. Pat. No. 4,446,232, which is incorporated herein by reference, particularly the use of mobile labeled antibody and immobilized ligand. The mobile labeled anti-albumin of the instant invention can be labeled with an enzyme, such as those taught by Liotta, including horseradish peroxidase, alkaline phosphate, and beta-galactosidase, as well as other enzymes well known in the art which are useful for generating a color or other signals. Alternatively, other labels, such as sol particles, for example, gold sol, latex, or other labels capable of producing a signal which are well known in the art can be used.

The glycated albumin binding layer can be, for example, antibodies specific for the conjugates of glycated albumin bound to anti-albumin. Alternatively, the glycated albumin binding layer can comprise materials well known for binding glycated proteins, such as phenyl boronic acids as described above and in U.S. Pat. No. 4,269,605 to Dean and U.S. Pat. No. 5,284,777 to Rosenthal et al., each of which is incorporated herein by reference. As mentioned above, phenyl boronic acid binds to the cis-diol groups in a glucose-modified protein to form a reversible five-membered ring complex. The boronic acid can be coupled to the layer of the test strip through an agarose or cellulose matrix or by other methods and materials well known in the art, such as those described in the above-identified patents.

In yet another embodiment the PBG test device is a multi-layer test device for analyzing fructosamine concentration. The multi-layer test device contains a signal producing system which is an indicator capable of being reduced by fructosamine such as certain dyes, including chromogenic dyes, or fluorescent reagents. The multi-layer test device is described more fully below and in U.S. patent application Ser. No. 08/269,351, which is incorporated herein by reference.

Fructosamine Multi-Layer Test Device

The Multi-Layers: The layers of the multi-layer test device are positioned adjacent to each other so that they provide for fluid communication. The fluid flow between the adjacent layers can be either vertical or lateral. Accordingly, the layers of the multi-layer device can be superposed or juxtaposed.

The various multi-layers of the test device contain the assay reagents of interest, such as a buffer or an indicator. The reagent of interest can be impregnated into the layer or coated into or onto a layer or covalently attached to the layer.

The material for the various layers described herein, including the buffer layer, the indicator layer, and any additional layers, comprise a porous matrix which is capable of containing the assay reagent of interest but which is permeable to the fructosamine analyte and other critical assay reagents and liquids. The permeability generally arises from porosity, ability to swell or any other characteristic. The test device layers can comprise various porous, fibrous materials such as cellulose, papers, fleeces, felts, woven fabric and the like (see, for example, U.S. Pat. Nos. 3,802, 842; 3,809,605; and 3,897,214, all of which are incorporated herein by reference). Alternatively, the test device layers can comprise porous, non-fibrous materials, such as microporous polymers (see, for example, U.S. Pat. No. 3,552,929, which is incorporated herein by reference). Specific examples of suitable materials which can be used for the layers include filter paper, such as 3 mm filter paper (Whatman, Maidenstone, England), Rayon, Cytosep® membrane (Ahlstrom Filtration, Inc., Mt. Holly Spring, Pa.), glass fiber, and Biodyne A® nylon membrane (Pall Corp., East Hills, N.Y.).

The multiple layers containing the assay reagents, such as buffer or indicator, can be assembled simultaneously or sequentially. The porous material for a given layer is first placed in a solution of assay reagent such as a buffer solution or an indicator solution. After drying, the layer can be stored in a desiccator cabinet until it is ready for use in the multi-layer test device.

The multi-layers are generally in the form of reagent pads which are mounted onto one support member or sandwiched between two or more support members as discussed more fully below. The multi-layer pads can be any geometrical dimension, such as circular or rectangular, and are generally 0.5 to 20 mm in circumference, preferably 1 to 10 mm, and are positioned either superposed or juxtaposed relative to each other.

Regardless of the multi-layer positioning, the test devices which can be used in the present invention to analyze fructosamine comprise the basic elements of a buffer layer, an indicator layer and can contain additional layers as described below.

Buffer Layer: The buffer layer 13 contains a buffer having a pH value of at least 9. Various known types of buffers can be contained in the buffer layer as long as the buffer provides sufficiently high pH such that the fructosamines are converted to their eneaminol form. To achieve this, the pH of the buffer should be at a pH value between about 9 and about 13, and for optimum results the pH is at a pH value of between 10 and 12. Examples of such buffers include potassium hydrogen phosphate, sodium hydrogen phosphate, sodium hydroxide, guanidinium salts, certain amino acids, and other suitable buffers as are well known in the art, or combinations thereof. Where the buffer layer is superposed above the indicator layer it is generally of a non-opaque, liquid-permeable material.

Indicator Layer: The indicator layer 14 contains any indicator capable of being reduced by fructosamine such as certain dyes, including chromogenic dyes, or fluorescent reagents. Examples of suitable chromogenic dyes which change color based on the amount of fructosamine present in a liquid sample include tetrazolium dyes such as Neotetrazolium chloride (NT), Tetranitroblue tetrazolium chloride (TNBT), Blue tetrazolium chloride (BT), Iodonitrotetrazolium chloride, Nitroblue tetrazolium chloride (NBT), Nitro Blue Monotetrazolium Chloride, Thiazolyl blue tetrazolium bromide (MTT), Tetrazolium violet, 2,3,5-Triphenyl-2-H-tetrazolium chloride, Thiocarbamyl nitro blue tetrazolium chloride (TCNBT), Tetrazolium XTT (XTT), 2-2'-Benzothiazolyl-5-styryl-3-(4'-phthalhydrazidyl) tetrazolium chloride (BSPT), Distyryl nitroblue tetrazolium chloride (DSNBT). An example of a suitable fluorescent reagents is 5-Cyano-2,3-ditolyl tetrazolium chloride (CTC).

Figure 2:
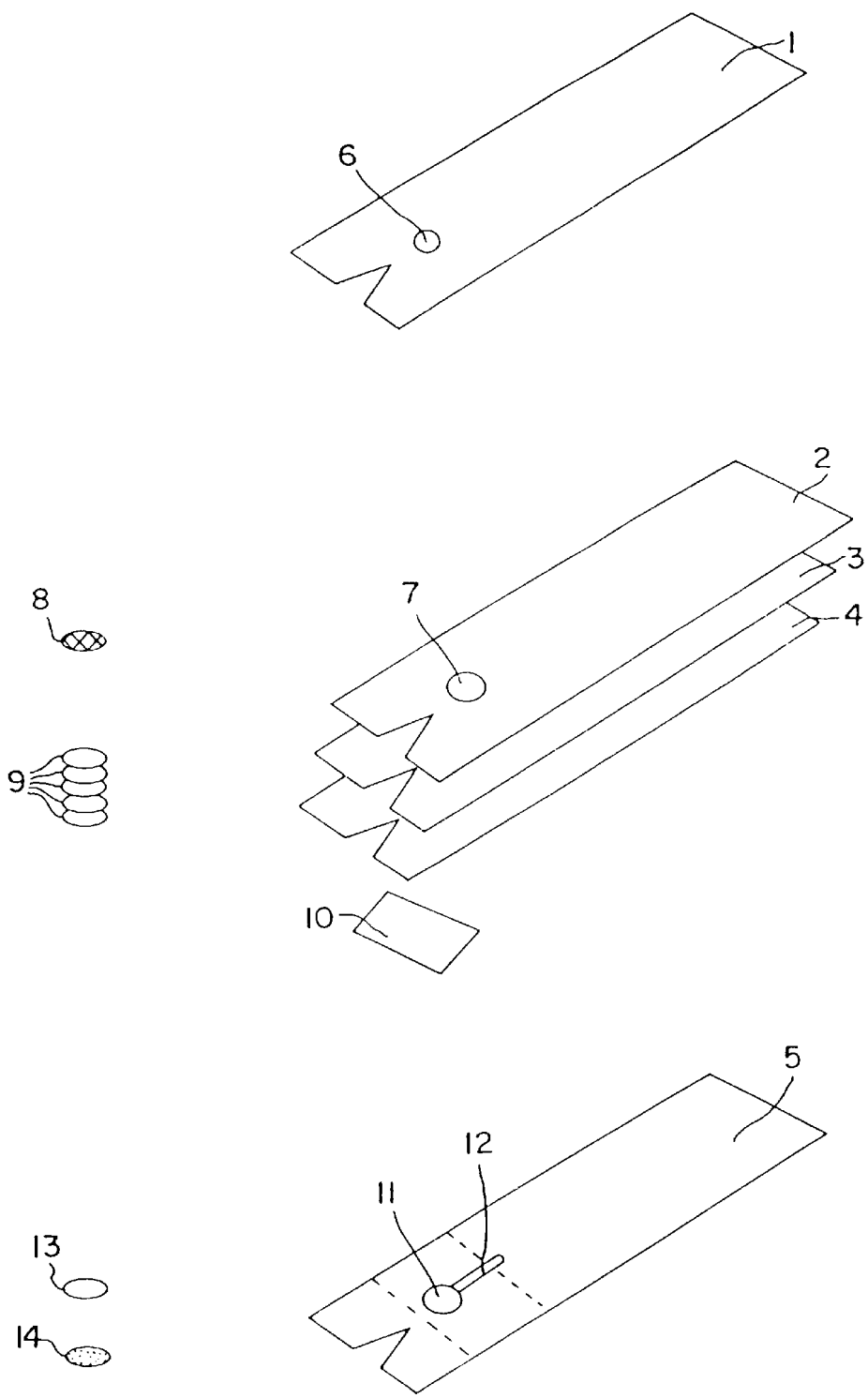
FIG. 2 depicts one embodiment of a multi-layer test device which can be used for measuring the concentration of fructosamine in a body fluid sample.

Additional Layers: Other layers, in addition to the buffer layer and the indicator layer, can be used in the fructosamine test device. For example, the multi-layer test device can include a red blood cell (RBC) separation layer or layers before the buffer layer pad, for the purpose of separating RBC components, for example as shown in FIG. 2, items 8 and 9 and as described in the Examples. Other useful layers, include, but are not limited to, those described in U.S. Pat. Nos. 4,050,898 and 4,042,335, which are incorporated herein by reference, including radiation blocking layers, interference removal layers which can contain detergents, chelators, anti-oxidants, or other substances which can interfere with accurate results, contamination prevention layers, dialysis layers, filtering layers, support layers and the like.

Supporting The Multi-Layers: The support member or members which hold the multi-layers can be opaque, reflective, or transparent to light or other energy. The support member(s) will be compatible with the intended analysis mode and indicator used (such as chromogenic or fluorescence indicators). Materials that can be used for the support members include a variety of plastics and polymers such as cellulose acetate, polyester, polycarbonate, polyvinylchloride, polyethylene, and polystyrene. Generally, where such materials are used, the support member is substantially planar. The layers can also be housed in a plastic container which holds layers in their proper orientation or they can be housed in other supports known in the art, such as the ICON device (Hybritech, Inc., San Diego, Calif.).

The multi-layer device has at least one support member optionally having a detection aperture. As used herein the phrase "optionally having a detection aperture" means that where the one support member is transparent, there is no need for a detection aperture whereas with a non-transparent support member a detection aperture is needed and present. The detection aperture is a hole for observing the color transition or fluorescence on the indicator layer. The size of the aperture is generally smaller than the size of the multi-layers and its size depends on the size of the layer or layer pads. The aperture size will generally be from 0.5 to 20 mm, preferably between 1 and 10 mm. The position of the detection aperture on the bottom support member depends upon whether the multi-layers are superposed or juxtaposed. Where the multi-layers are superposed, the detection aperture is below all of the multi-layers. Where the multi-layers are juxtaposed, the detection aperture is directly below only the indicator layer or other final layer.

Where only one support is used, the liquid sample can be applied directly to the first multi-layer. The liquid sample freely permeates and diffuses into and flows through the buffer layer, and any additional layer present, and migrates to the indicator layer such that the concentration of fructosamine can be determined.

While only one support as described above can be necessary, additional supports can be used. Where two or more supports are used, the multi-layers are sandwiched between a first support member having a sample aperture and a second support member optionally having a detection aperture. Like the detection aperture, the sample aperture is generally of a size less than the size of the multi-layers and its size depends to a large extent on the size of the layer or layer pads. The aperture size will generally be from 0.5 to 20 mm, preferably between 1 and 10 mm.

The two or more support members can be held together by a securing means, such as adhesive. Examples of adhesive that can be used include gelatin, rubber, silicone, and acrylate base glue. In addition, the plastic housing can be sonically welded or snapped together as is common in the state of the art.

One embodiment of the multi-layer test device used in determining the concentration of fructosamine is shown in FIG. 2. With reference to FIG. 2, the embodiment has an outer first plastic substantially planar support member 1 having a sample aperture 6 and an outer second plastic substantially planar support member 5 which has a detection aperture 11 and groove 12. The embodiment contains additional support members 2, 3, and 4 which have a hole 7 for fluid communication. The additional support members house whole blood separation layers 8, 9, and 10 as described more fully in the ensuing Examples. Supported by the outer second support member 5 is a non-opaque, liquid-permeable buffer layer pad 13 containing a buffer having a pH value of between about 10 and about 12 which is superposed above an indicator layer pad 14 containing a nitroblue tetrazolium dye.

Figure 4:
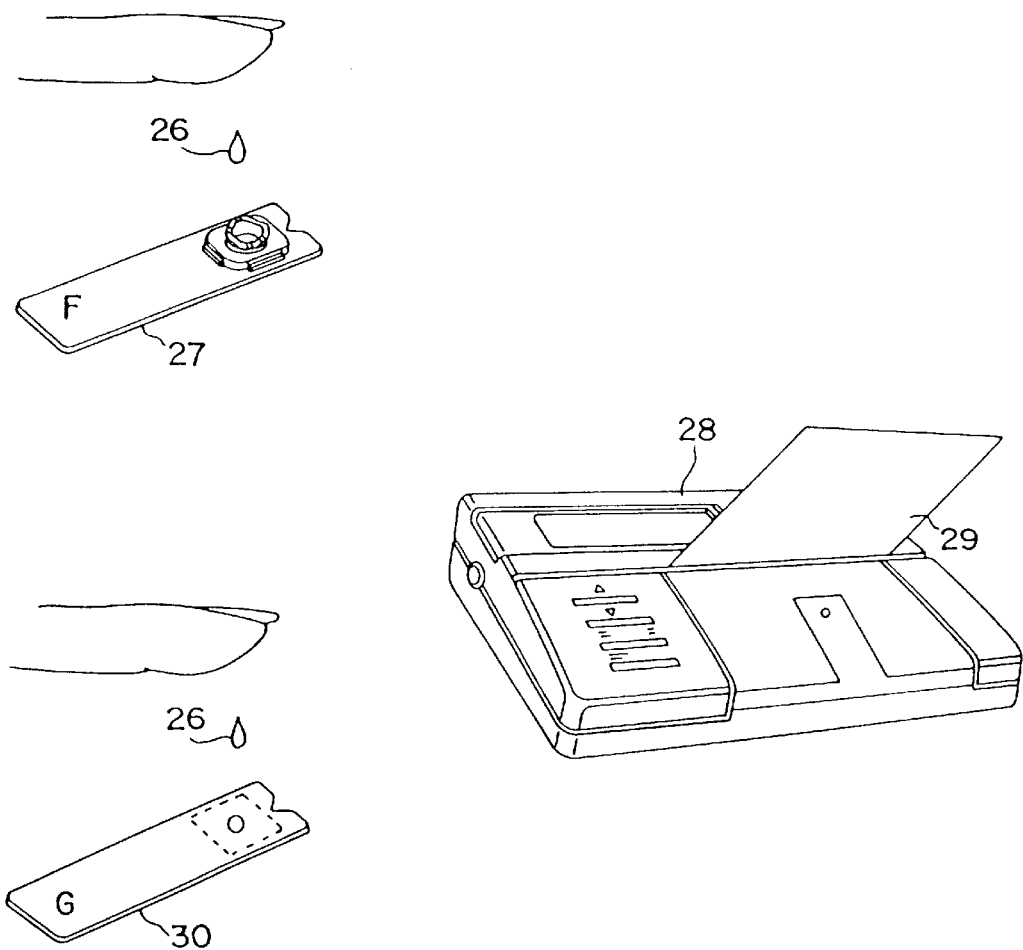
FIG. 4 depicts a body fluid sample being applied to a fructosamine (F) and a glucose (G) test device.

A body fluid sample containing the analyte to be measured is applied to the appropriate test device which contains a reagent designed to interact with the analyte in a specific way so that a measurable signal is produced, as described above. After the body fluid sample is applied to the appropriate test device, the concentration of glucose or PBG in the body fluid sample can be determined with an apparatus 29, such as that exemplified in FIG. 4 and described more fully below. The apparatus has automatic glucose and PBG concentration determining means that are responsive to the signal produced from the reactions of glucose and PBG with the signal producing systems of the respective test device. The apparatus also has a display means 28 coupled to the automatic determining means as well as receiving port in connection with the automatic determining means. Since the present invention is advantageously used in the home environment, the apparatus and test should be portable. For example, the apparatus used in the test system can be battery operated.

A suitable apparatus used in the single test system can read the results of both the glucose test and the PBG test and is therefore termed a "glycemic measuring apparatus". Such apparatus will be constructed to specifications which are dependent upon the signal producing system of the test and the automatic determining means which is responsive to the signal produced. For example, if the automatic concentration determining means, or read-out, is color production, the apparatus can contain a determining means which is a spectrometer. Other spectrophotometers which can be used with the present invention can measure, for example, fluorescence, absorbance, or transmittance. If the read-out is electrochemical, a miniaturized electrode system can be employed. For example, it is well known in the art how to measure glucose electrochemically, as taught, for instance, by Higgins et al. in U.S. Pat. No. 4,545,382, Parks et al. in U.S. Pat. No. 4,999,582, and White in U.S. Pat. No. 5,243,516, each of which is incorporated herein by reference. More than one automatic determining means can be present in the apparatus. For example, an electrode can be present for measuring the concentration of glucose and a reflectance spectrometer can also be present in the apparatus for measuring the concentration of fructosamine. A detailed description of a reflectance spectrometer for measuring glucose and fructosamine is presented below. However, other apparatus can be constructed which can measure both glucose and glycated proteins.

Figure 3B:
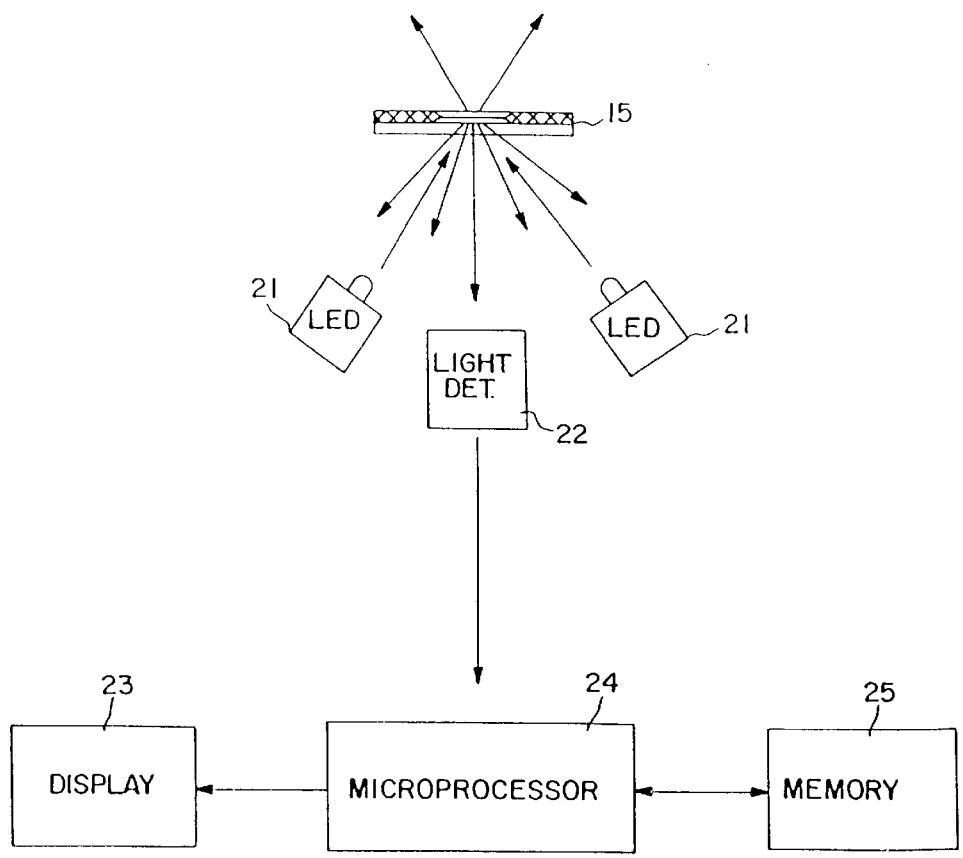
FIG. 3b is a block diagram schematic of an apparatus that can be used in the practice of the present invention.

In the glycemic measuring apparatus a suitable automatic glucose and PBG concentration determining means, such as a reflectance spectrophotometer with appropriate software, can be made to automatically read reflectance at certain points in time, calculate rate of reflectance change, and, using calibration factors, output the level of analyte in the blood sample. Such a device is schematically shown in FIG. 3b wherein test devices of the present invention can be measured. Light source 21, for example a high intensity light emitting diode (LED), projects a beam of light onto the reading area of the test device 15. A portion of this light is diffusively reflected from the reading area and is detected by light detector 22, for example a light to frequency converter that produces an output frequency proportional to the light it receives.

Light source 21 and/or detector 22 can be adapted to generate or respond to specific wavelengths of light, if desired. The light source can be polychromatic and the light detector capable of measuring two or more different wave lengths. Alternatively, or in addition thereto, the glycemic measuring apparatus can have two or more LED sources capable of emitting two or more distinct wavelengths of light. For example, in a preferred embodiment, the apparatus contains two LED sources, both by Stanley Electronic Company (Irvine, Calif.), identified as MPG 3368S and MVR3368S. Commercially available light to frequency converters include those made by Texas Instruments (Houston, Tex.) and identified as TSL235, and the preferred component, TSL230.

The output of detector 22 is processed by a microprocessor 24 for data processing. The microprocessor 24 can serve the following control functions: (1) timing for the entire system; (2) processing the frequency data from the light to frequency converter; (3) calculating analyte levels from the stored reflectance; and (4) outputting analyte concentration data to display 23. Numerous microprocessors can be used, such as the DS5000T by Dallas Semiconductor Company (Dallas, Tex.). A memory circuit 25 can store data and the microprocessor operating program. The display means 23 can take various hard copy and soft copy forms. Usually it is visual display, such as liquid crystal (LCD) or LED display, but it can be a tape printer, audible signal, or the like. The instrument also can include a start-stop switch and can provide an audible or visible time output to indicate for applying samples, taking readings etc., if desired.

Although other methods of taking measurements are possible, the following method has provided the desired results. Readings are taken at specified intervals after the timing is initiated. The intervals may vary depending upon which concentration is being measured. For example, the PBG intervals may be every 15 seconds whereas the glucose readings may be every 5 seconds. Measurements are performed by powering the LED for a brief period of time. During this time span, the reflected light is converted to a frequency by the light to frequency converter. This conversion is monitored by the microcomputer by counting the pulse-width produced by the light to frequency converter. These raw reflectance readings are defined in counts for the output pulse-width. The counts are then used for calculations performed by the microprocessor to compute the concentrations of glucose or PBG.

The glycemic measuring apparatus can also have a temperature sensor which senses the ambient temperature and temperature changes. The sensor is particularly useful to account for temperature dependent changes in test reactivity. A digital thermometer which can satisfactorily monitor ambient temperature and temperature changes can be employed. The Dallas Semiconductor temperature sensor DS1620 has proven useful for this application.

As discussed above with reference to the temperature sensor, the analysis for glucose and PBG with the instant invention can be done at ambient temperature or room temperature (approximately 20° C.). Surprisingly, and unexpectedly, even at ambient temperature and without a reaction accelerator, the present invention is capable of analyzing fructosamine concentration levels in less than or equal to about five minutes, and even in as little time as about four minutes or less, and preferably, about three minutes or less, as shown by the Examples below. The prior art either uses reaction accelerators or elevated temperatures. For example, Ismail's dry-phase fructosamine assay, described in U.S. Pat. No. 4,956,301, requires the use of a reaction accelerator compound to analyze fructosamine levels at ambient temperature. As used herein "reaction accelerator" means any compound added solely for the purpose of accelerating the reaction of the fructosamine assay. Such compounds are, generally, nonionic surfactants and organic solvents which speed the reaction rate of the fructosamine assay. The methods of the present invention of analyzing fructosamine in about five minutes or less exclude the use of such reaction accelerators.

In addition, as mentioned above, elevated temperatures are also used in prior art methods for accelerating the fructosamine assay. For example, Sakamoto's multi-layer analytical element for analyzing fructosamine, described in published European Patent Application 0 473 109, requires elevated temperatures on the order of 37–40° C., as does the fructosamine assay described in U.S. Pat. No. 5,370,990 to Staniford et al. With the instant invention elevated temperatures are not required to achieve complete fructosamine analysis in about five minutes or less.

The following examples are intended to illustrate but not limit the invention.

EXAMPLE I

This Example provides the preparation and testing of a protein-bound glucose, fructosamine, with a whole blood sample.

Preparation of Fructosamine Test Device
Blood Separation Portion of Fructosamine Test Device
Tetko mesh #7–280/44 (Tetko, Inc. Rueschlikon, Switzerland) was placed in a detergent solution of 1%

Pluronic (Pragmatics, Inc., Elkhart, Ind.) for 1 minute. Excess detergent was removed and the mesh was dried by heating at 60° C. for 10 minutes. Mesh was stored in desiccated plastic bags until ready for use at which time ³⁄₁₆" circles were placed in the multi-layer test device on support member 2 (FIG. 2).

Cytosep® membrane #1661 (Ahlstrom Filtration, Inc., Mt. Holly Spring, Pa.) was placed for 1 minute in a phosphate buffered saline (PBS) solution containing 300 ug/ml potato lectin (Sigma Chemical Co., St. Louis, Mo.). Excess solution was removed and the membrane was dried for 60 minutes at 40° C. After drying, the blood separation layer membrane was stored in desiccated plastic bags. When ready for use, five (5) ³⁄₁₆" circles of membrane were placed in the multi-layer test device between support members 2, 3, and 4 (FIG. 2).

An untreated polycarbonate membrane of 0.4 $\mu$m pore size (Corning Costar, Cambridge, Mass.) was cut into a 1 cm square and adhered to the bottom of plastic support member 4 covering the ³⁄₁₆" opening.

Signal Producing Portion of Fructosamine Test Device

Buffer Layer Pad: Schleicher and Schuell type 589 paper (Keene, N.H.) was placed for 1 minute in a 1.0 molar solution of guanidinium carbonate buffer (Sigma Chemical Co., St. Louis, Mo.), pH 11.5, containing 1% Pluronic detergent (Pragmatic Inc., Elkhart, Ind.). Excess buffer was removed and the paper was dried for 30 minutes at 60° C. After drying, the buffer layer paper was stored in a desiccator cabinet. When ready for use, a ³⁄₁₆" circle of buffer paper was placed in plastic support member 5.

Indicator Layer Pad: Ahlstrom A131 glass fiber (Ahlstrom Filtration Inc., Mt. Holly Spring, Pa.) was placed in an aqueous solution of 5 millimolar nitroblue tetrazolium chloride (NBT) (Sigma Chemical Co., St. Louis, Mo.) for 1 minute. Excess NBT was removed and the glass fiber was dried at 60° C. for 30 minutes. After drying, the glass fiber was stored in the dark. When ready for use, a ³⁄₁₆" circle of NBT glass fiber was placed on plastic support member 5.

Support Members

Five white polystyrene substantially planar strips (LXN Corp., Irvine, Calif.) were used. The bottom strip 5 had a ³⁄₁₆" diameter opening with a 1 mm by 7 mm groove covered by a 0.002 inch thick polyethylene window adhered to the bottom of the strip. The middle three strips 2, 3, and 4 had ³⁄₁₆ inch diameter openings with adhesive on the bottom of each strip. The top strip 1 had a ⅛ inch diameter opening with adhesive on the bottom of the strip.

Assembly of the Multi-layer Fructosamine Test Device

The blood separation portion of the test device and the signal producing portion of the device were assembled as shown in FIG. 2. The mesh layer was placed on top of the five layers of lectin impregnated Cytosep® inside the three plastic supports that are adhered together. The plastic support with the ⅛ inch hole was placed on top of the three adhered plastic supports containing the mesh and Cytosep® layers. A 1 cm square of the polycarbonate was adhered to the bottom side of the three adhered plastic supports.

One buffer layer pad was superposed above one NBT indicator layer pad in the opening of the bottom plastic support member and which was pressed against the window adhered to the bottom of this plastic support member. The plastic support member containing the buffer layer and the indicator layer was adhered to the blood separation portion with the buffer layer pad superposed under the polycarbonate membrane and adhered by the adhesive on the bottom of the plastic support member 4.

Analysis of Fructosamine in Whole Blood Sample

Glycated human serum glycated albumin (G-HSA) was prepared by incubating 3 grams of HSA (Sigma Chemical Co. St. Louis, Mo.) in 20 mls of PBS containing 0.5 molar glucose at 45° C. for 14 days. The G-HSA was separated from unreacted glucose by elution over a column of Bio-Gel P-10 resin in PBS.

Samples of whole blood from a single individual were mixed with an equal volume of either PBS or a sample of G-HSA containing 6 millimolar fructosamine. Since the whole blood sample itself contained 2 millimolar fructosamine, the three samples contained 1, 2 and 4 millimolar fructosamine. Fifteen (15) microliters of each sample was tested with the fructosamine multi-layer test device described above. After addition of the sample, the test device was placed into a glycemic measuring apparatus as described above and the reflectance at 555 nm monitored for 3 minutes. The change in reflectance ($\blacktriangle$K/S) from 2 minutes to 3 minutes gave the following results:

| Sample | Fructosamine conc. | ▲K/S from 2 min to 3 min |
|---|---|---|
| Blood + PBS | 1 mM | 0.050 |
| Blood only | 2 mM | 0.075 |
| Blood & G-HSA | 4 mM | 0.110 |

As can be seen from the results, the reaction rate increased as the fructosamine concentration in the blood sample increased.

EXAMPLE II

This Example provides the preparation and testing of a rapid glucose test with a whole blood sample.

Preparation of Glucose Test Strips

A sheet of 0.8 micron Supor® membrane (Gelman Science, Ann, Arbor, Mich.) was dipped into a solution comprising:

| | |
|---|---|
| Gelatin-150 Bloom | 0.5 g |
| Glucose Oxidase | 0.285 g |
| Horse Radish Peroxidase | 0.133 g |
| Citric Acid | 0.593 g |
| Sodium Citrate | 2.61 g |
| Distilled Water | 32 ml |

After dipping, the sheet was dried in an oven at 56° C. for 20 minutes. The sheet was then dipped into a solution comprising:

| | |
|---|---|
| Isopropyl alcohol | 39.5 ml |
| 3,5,3',5'-Tetramethylbenzidine | 0.2 g |
| ortho-Tolidine | 0.2 g |
| Pluronic L64 (20%) | 0.5 ml |

After dipping, the sheet was dried at 56° C. for an additional 20 minutes. FIG. 3a shows the construction of a glucose test device 19. The glucose test membrane 18 described above was cut into 1 cm squares and adhered with adhesive 17 to a plastic holder 16 with a 5 mm hole 20 and a triangular notch 19. Blood samples were applied to the 5 mm hole 20. The samples wet the membrane and reacted to generate color in proportion to the glucose in the blood sample.

Analysis of Glucose in Blood Samples

Varying concentrations of glucose were added to a blood sample. A drop of each sample was added to a glucose test strip and the reflectance (▲K/S) was measured in a glycemic measuring apparatus, as described above, at 45 seconds. The following results were obtained:

| Glucose Concentration (mg/dL) | ▲K/S at 45 seconds |
|---|---|
| 82 | 0.198 |
| 208 | 1.380 |
| 339 | 2.347 |
| 430 | 3.270 |
| 657 | 4.373 |

The data demonstrate that the color produced was proportional to the glucose concentration in the blood sample.

Although the invention has been described with reference to the disclosed embodiments, those skilled in the art will readily appreciate that the specific examples detailed are only illustrative of the invention. It should be understood that various modifications can be made without departing from the spirit of the invention. Accordingly, the invention is limited only by the following claims.

We claim:

1. Method for determining the long-term integrated glycemic condition of a subject with a single test device responsive to a signal producing system indicative of glucose concentration and a signal producing system indicative of glycated protein concentration, consisting of the steps of:
   (a) applying a body fluid sample to a first test strip containing a signal producing system indicative of glucose concentration present in the body fluid sample;
   (b) applying a body fluid sample to a second test strip containing a signal producing system indicative of glycated protein concentration present in the body fluid sample; and
   (c) determining in either order (1) the glucose concentration and (2) the glycated protein concentration present in the body fluid sample applied to the first and second test strips, respectively,
      using a single test device having a glucose concentration determining means that is responsive to the signal producing system indicative of glucose concentration and
      a glycated protein concentration determining means that is responsive to the signal producing system indicative of glycated protein concentration,
      said test device preset to be responsive to only these two means, said test device further having an automatic determining means coupled to a display means and further having a receiving port for a test strip in connection with the automatic determining means;
   wherein the glucose concentration and the glycated protein concentration indicate long-term integrated glycemic condition of a subject.

2. The method of claim 1, wherein the body fluid sample of step (a) and the body fluid sample of step (b) are whole blood.

3. The method of claim 1, wherein the body fluid sample of step (a) and the body fluid sample of step (b) are separate body fluid samples.

4. The method of claim 1, wherein the glycated protein is glycated hemoglobin.

5. The method of claim 4, wherein the glycated protein is glycated hemoglobin $A_0$.

6. The method of claim 4, wherein the glycated protein is glycated hemoglobin $A_2$.

7. The method of claim 4, wherein the glycated protein is glycated hemoglobin F.

8. The method of claim 4, wherein the glycated protein is glycated hemoglobin $A_1$.

9. The method of claim 8, wherein the glycated protein is glycated hemoglobin $A_{1a1}$.

10. The method of claim 8, wherein the glycated protein is glycated hemoglobin $A_{1a2}$.

11. The method of claim 8, wherein the glycated protein is glycated hemoglobin $A_{1b1}$.

12. The method of claim 8, wherein the glycated protein is glycated hemoglobin $A_{1b2}$.

13. The method of claim 8, wherein the glycated protein is glycated hemoglobin $A_{1b3}$.

14. The method of claim 8, wherein the glycated protein is glycated hemoglobin $A_{1c}$.

15. The method of claim 8, wherein the glycated protein is glycated hemoglobin $A_{1d}$.

16. The method of claim 8, wherein the glycated protein is glycated hemoglobin $A_{1e}$.

* * * * *